(12) United States Patent
Patil et al.

(10) Patent No.: US 8,455,415 B2
(45) Date of Patent: Jun. 4, 2013

(54) POLY(ALPHA-OLEFIN/ALKYLENE GLYCOL) COPOLYMER, PROCESS FOR MAKING, AND A LUBRICANT FORMULATION THEREFOR

(75) Inventors: Abhimanyu Onkar Patil, Westfield, NJ (US); Satish Bodige, Wayne, NJ (US); Suzzy Chen Hsi Ho, Princeton, NJ (US); Thomas Francis Degnan, Moorestown, NJ (US); David Joseph Baillargeon, Cherry Hill, NJ (US); Margaret May-Som Wu, Skillman, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 578 days.

(21) Appl. No.: 12/589,489

(22) Filed: Oct. 23, 2009

(65) Prior Publication Data

US 2011/0098204 A1   Apr. 28, 2011

(51) Int. Cl.
*C10M 145/24* (2006.01)

(52) U.S. Cl.
USPC .................... 508/591; 508/579; 525/910

(58) Field of Classification Search
USPC .............................................. 508/579
See application file for complete search history.

(56) References Cited

U.S. PATENT DOCUMENTS

| | | | |
|---|---|---|---|
| 3,475,395 A * | 10/1969 | Hsieh ........................... 528/393 |
| 3,634,244 A | 1/1972 | Herold et al. |
| 3,933,861 A | 1/1976 | Kurkov |
| 6,087,307 A | 7/2000 | Kaminski et al. |
| 6,232,279 B1 | 5/2001 | Steigerwald |
| 6,462,154 B1 * | 10/2002 | Naganuma et al. ........... 526/153 |
| 6,566,566 B1 | 5/2003 | Maas et al. |
| 2002/0183465 A1 | 12/2002 | Babcock et al. |
| 2003/0010495 A1 | 1/2003 | Mendez et al. |
| 2003/0017674 A1 | 1/2003 | Miles et al. |
| 2005/0023427 A1 | 2/2005 | Chen et al. |

FOREIGN PATENT DOCUMENTS

| | | |
|---|---|---|
| CN | 1566170 | 6/2003 |
| GB | 1436763 | 5/1976 |
| JP | 2004223389 A | 1/2003 |
| JP | 20052257 | 2/2004 |
| JP | 2005298443 | 4/2004 |
| SU | 1031972 A | 5/1981 |
| WO | 0168765 A2 | 9/2001 |
| WO | 2007/146081 A1 | 12/2007 |

OTHER PUBLICATIONS

Rubber—Chemistry Encyclopedia, Jan. 2012.*

* cited by examiner

*Primary Examiner* — Taiwo Oladapo
(74) *Attorney, Agent, or Firm* — Robert A. Migliorini

(57) ABSTRACT

A poly(alpha-olefin/alkylene glycol) copolymer of the following formula:

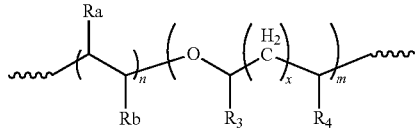

wherein $R_3$, $R_4$, Ra, and Rb are, independently, any of H, a $C_1$ to $C_{18}$ normal or branched alkyl radical, or a $C_1$ to $C_{18}$ aromatic radical or aromatic-containing alkyl radicals; wherein n and m, are, independently, integers from 1 to 1000; and wherein x is an integer from 0 to 10. There is also a process for making the copolymer. There is also a lubricant formulation having the copolymer.

10 Claims, No Drawings

POLY(ALPHA-OLEFIN/ALKYLENE GLYCOL) COPOLYMER, PROCESS FOR MAKING, AND A LUBRICANT FORMULATION THEREFOR

FIELD

The present disclosure relates to copolymer useful as a lubricant or engine oil. The present disclosure further relates to a process for making the copolymer. The present disclosure further relates to a lubricant formulation having the copolymer therein.

BACKGROUND

Poly(alpha-olefin) (PAOs) fluids are commercially employed as base stocks in lubricant products. PAOs have many advantages compared to conventional mineral oils and Group III/III+ lubricants. More specifically, PAOs have superior VI (viscosity index), low temperature properties (CCS, MRV, etc.), pour points, and low traction, which translates into better energy efficiency and additive response and complete miscibility in conventional mineral oils. Performance limitations of PAOs include a lack of polarity, which impacts ability to solubilize polar additives, such as antioxidants, anti-rust agents and anti-wear agents. Conventionally, polar organic esters have been added to PAO lubricants to render them compatible. Useful commercial formulations may have 2% or more of such esters in a fully homogeneous lubricant blend. Examples of such esters include, for example, bis-tridecanol adipate and pentaerythritol hexanoate.

Polyalkylene glycol (PAG) fluids have also been employed as lubricant base stocks. Their performance advantages are high VI, good lubricity (in hydrodynamic, mix, and boundary lubrication conditions), and excellent cleanliness. Some grades are even considered acceptable for incidental food contact (H1 grade). Performance limitations include lack of miscibility and compatibility with conventional mineral and hydrocarbon-based lubricants as well as high solubility in water, which results in severe corrosion problem. Some PAGs have paint or seal compatibility problems. The formulation or additive response of PAGs with respect to additives can be unpredictable, rendering them difficult to formulate with.

It would be desirable to have lubricant base stocks that had the performance advantages of both PAOs and PAGs without their limitations. It would also be desirable to have lubricant base stocks that can be readily blended with conventional lubricant base stocks.

SUMMARY

According to the present disclosure, there is provided a poly(alpha-olefin/alkylene glycol) copolymer of the following formula:

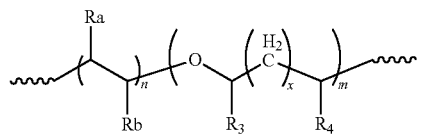

wherein $R_3$, $R_4$, Ra, and Rb are, independently, any of H, a $C_1$ to $C_{18}$ normal or branched alkyl radical, or a $C_1$ to $C_{18}$ aromatic radical or aromatic-containing alkyl radicals; wherein n and m, are, independently, integers from 1 to 1000; and wherein x is an integer from 0 to 10.

Further according to the present disclosure, there is provided a lubricant formulation. The formulation has a first lubricant base stock of the copolymer described above and a second lubricant base stock different than the first base stock.

According to the present disclosure, there is provided a process for making a poly(alpha-olefin/alkylene glycol) copolymer by reacting an alpha-olefin and an alkylene glycol in the presence of a Lewis acid according to the following sequence:

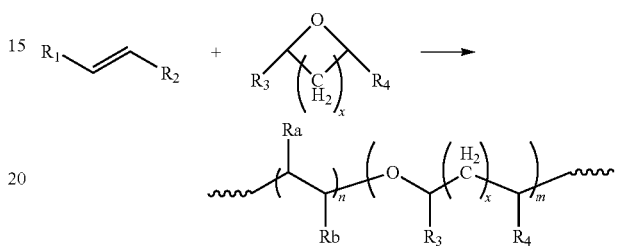

wherein $R_1$, $R_2$, $R_3$, $R_4$, Ra, and Rb are, independently, any of H, a $C_1$ to $C_{18}$ normal or branched alkyl radical, or a $C_1$ to $C_{18}$ aromatic radical or aromatic-containing alkyl radicals; wherein n and m, are, independently, integers from 1 to 1000; and wherein x is an integer from 0 to 10.

DETAILED DESCRIPTION

All numerical values within the detailed description and the claims herein are modified by "about" or "approximately" the indicated value, and take into account experimental error and variations that would be expected by a person having ordinary skill in the art.

In this present disclosure, the poly(alpha-olefin/alkylene glycol) copolymer has both alpha-olefin monomeric content and alkylene glycol monomeric content. The copolymer exhibits the performance attributes of each of conventional PAO and PAG fluids without the performance limitations of each.

The copolymer of the present disclosure takes the form of a poly(alpha-olefin/alkylene glycol) as shown in the following structure:

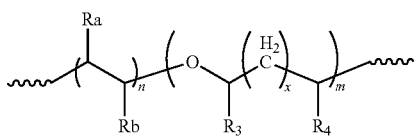

wherein $R_3$, $R_4$, Ra, and Rb are, independently, any of H, a $C_1$ to $C_{18}$ normal or branched alkyl radical, or a $C_1$ to $C_{18}$ aromatic radical or aromatic-containing alkyl radicals; wherein n and m, are, independently, integers from 1 to 1000; and wherein x is an integer from 0 to 10. Preferably, n and m, are, independently, integers from 1 to 500. Most preferably, n and m, are, independently, integers from 2 to 400. Preferably, x is an integer from 0 to 5.

Alpha-olefins (α-olefins) useful as comonomers include ethylene and linear or branched $C_3$ to $C_{20}$ α-olefins. Examples of useful $C_3$ to $C_{20}$ α-olefins include propylene, 1-butene, 1-pentene, 1-hexene, 1-heptene, 1-octene, 1-nonene, 1-decene, 1-undecene, 1-dodecene, 1-tetradecene or 1-hexadecene. A most preferred α-olefin is 1-hexene to 1-tetradecene. The olefin can be a single olefin or a combination of two or more olefins.

The alkylene glycol fractions of the formula are derived from alkylene oxide (AO) or epoxide monomers. Useful AO monomers include those of $C_2$ to $C_{20}$ carbons, such as ethylene oxide, propylene oxide, 1,2-epoxybutane, 2,3-epoxybutane, 1,2-epoxydodecane, 1,2-epoxyhexadecane, 1,2-epoxyhexane, 1,2-epoxyoctane, 1,2-epoxypentane, 1,2-epoxytetradecane and a combination of two or more thereof. The epoxide can have a structure of a 4 to 5 member ring, such as those of 1,3-propylene oxide and 1,4-butyleneoxide(tetrahydrofuran). Formula A may contain a single AO or a mixture of two or more AOs.

A desirable embodiment of the compound is $R_1$=H and one of the hydrocarbon portions of the feed as an alpha-olefin or a combination of two or more alpha-olefins. Another desirable embodiment is x=0 and one of the oxygen-containing portions of the feed is ethylene oxide, propylene oxide, butylene oxide, higher alkylene oxides, 1,3-propylene oxide, 1,4-butylene oxide (tetrahydrofuran) or a combination of one or more of them.

The copolymer is preferably to have higher alpha-olefin monomeric content than alkylene oxide monomeric content. The copolymer preferably contains more than 5 mole % alpha-olefin units, more preferably more than 10 mole % alpha-olefin units, more preferably more than 20 mole % alpha-olefin units, more preferably more than 30 mole % alpha-olefin units, more preferably more than 40 mole % alpha-olefin units, more preferably more than 60 mole % alpha-olefin units, more preferably more than 70 mole % alpha-olefin units, more preferably more than 80 mole % alpha-olefin units, more preferably more than 90 mole % alpha-olefin units, or more preferably up to 99 mole % alpha-olefin units. The amount of alkylene oxide monomer units in the copolymer is preferably less than 90 mole %, more preferably less than 80 mole %, more preferably less than 70 mole %, more preferably less than 60 mole %, more preferably less than 50 mole %.

Alpha-olefin content is important in determining the compatibility of the copolymer with other hydrocarbon base stocks, especially API Gr I to Gr IV base stocks. Typically, copolymers with higher proportions of alpha-olefin units exhibit greater compatibility with the hydrocarbon base stocks. However, it is critical to have suitable proportions of alkylene oxide units, which impart greater polarity and improve frictional coefficient of the copolymer. Preferred copolymers have at least 10 mole % alpha-olefin content.

The copolymer of the disclosure is useful use as a lubricant base stock or a functional fluid and preferably has a 100° C. kinematic viscosity of 1.5 cSt to 3000 cSt according to ASTM D445 method. The copolymer has a 40° C. kinematic viscosity of 3 to 15000 cSt. Preferred copolymers exhibit a high viscosity index (VI). The VI typically ranges from 70 to 300 depending on viscosity, amount of alpha-olefin units, amount of alkylene oxide units, type of alpha-olefin or alkylene oxide units, method of synthesis, chemical compositions, and the like. Pour points are generally below −5° C. even in the case of the higher molecular weight oligomers with viscosities (100° C.) of 20 cSt or higher. Pour points (ASTM D97 or equivalent) generally range between −20 and −55° C. and usually below −25° C. Product viscosity may vary in view of factors such as copolymerization conditions, such as reaction temperature and reaction time. Higher temperatures and reaction times may result in higher molecular weight/higher viscosity products. The lubricant fraction of the product will typically be a 4 cSt to 3000 cSt (100° C.) material but low viscosity products 1.5 cSt to 40 cSt (100° C.) may also be obtained for use in lubricants in which a low viscosity base stock is desired.

The molecular weight of the copolymer typically ranges from 200 to 20,000, typically from 300 to 10,000, and most typically from 350 to 7,500. Higher molecular weights and corresponding viscosities may be achieved by suitable choice of reaction conditions. Values of the polydispersity index (PDI) are typically from 1 to 3.0.

The copolymer can take the form of a block copolymer or a random copolymer or combination of both. Block copolymers can take the form of a diblock copolymer, a multi-block, or a repeating block copolymer. The copolymer optionally may contain minor amounts of homopolymers or other polymers as long as a homogeneous mixture can be obtained. The word "copolymer" is not limited to only two monomer types, but also used to include polymers of more than two or three types of monomer units.

For automotive engine lubricant formulations, it is generally preferred to have lower viscosity fluids, e.g., below 10 cSt. Lower viscosity is known to impart lower viscous drag thus offering better energy efficiency or fuel economy. Both low viscosity and high viscosity fluids are useful in industrial lubricant formulations to yield different ISO vis grad lubricants. For industrial lubricant formulations, it is generally important to use fluids of high VI and high hydrolytic stability.

For both engine and industrial lubricant application, it is important to have a lubricant formulation with a low friction coefficient. Fluids with low friction coefficients exhibit low frictional loss during lubrication. Low frictional loss is critical for improved energy or fuel efficiency of formulated lubricants.

Friction coefficients can be measured by a High Frequency Reciprocating Rig (HFRR) test. The test equipment and procedure are similar to the ASTM D6079 method except the test oil temperature is raised from 32° C. to 195° C. at 2° C./minute, 400 g load, 60 Hz frequency, and 0.5 mm stroke length or 400 g load, 60 Hz frequency at constant temperature, such as 100° C. or 60° C. The test can measure average friction coefficient and wear volume.

The copolymer of the present disclosure may be formed by technique known in the art for copolymerization of alpha-olefins and alkylene glycols. Cationic or acid catalyzed polymerization or anionic (or base-catalyzed) polymerization are preferred methods to produce the copolymer. The copolymer can also be produced by radical polymerization using radical initiators. Furthermore, the copolymer can also be prepared by other synthetic, non-polymerization schemes.

A process of the present disclosure is shown in the following reaction sequence:

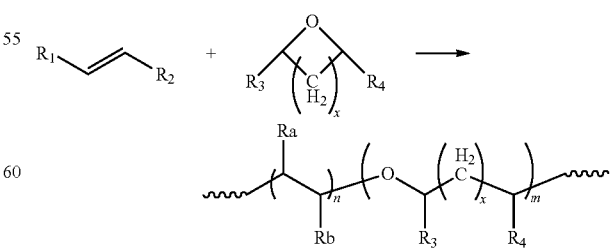

wherein $R_1$, $R_2$, $R_3$, $R_4$, Ra, and Rb are, independently, any of H, a $C_1$ to $C_{18}$ normal or branched alkyl radical, or a $C_1$ to $C_{18}$ aromatic radical or aromatic-containing alkyl radicals;

wherein n and m, are, independently, integers from 1 to 1000; and wherein x is an integer from 0 to 10.

The copolymerization of monomers can be carried out in the presence of a catalyst of a Lewis acid. Useful Lewis acid catalysts include metal and metalloid halides conventionally used as Friedel-Crafts catalysts, such as $AlCl_3$, $BF_3$, $AlBr_3$, $TiCl_3$, and $TiCl_4$ either alone or with a protic promoter. Solid Lewis acid catalysts, such as synthetic or natural zeolites; acid clays; polymeric acidic resins; amorphous solid catalysts, such as silica-alumina; and heteropoly acids, such as the tungsten zirconates, tungsten molybdates, tungsten vanadates, phosphotungstates and molybdotungstovanadogermanates (e.g., $WOx/ZrO_2$, $WOx/MoO_3$) may also be used although they are not generally as preferred as the metal and metalloid halides. In general, the acid catalyst used in the copolymerization process is 0.1 to 30 wt % and preferably 0.2 to 3 or 5 wt % based on total feed.

Lewis acid catalysts most frequently used for the copolymerization are the metal and metalloid halide catalysts. The catalysts most preferred in conventional PAO oligomerization processes are aluminum trichloride and boron trifluoride. Boron trifluoride is typically used in combination with a protic promoter. Promoters are well-known in $BF_3$-catalyzed olefin oligomerization processes include water, alcohols, such as the lower ($C_1$-$C_6$) alkanols, methanol, ethanol, isopropanol, and butanol; acids; organic acids, including carboxylic acids such as acetic acid, propionic acid, and butanoic acid; anhydrides of organic acids such as acetic anhydride; inorganic acids, such as phosphoric acid, and as further described in U.S. Pat. No. 3,149,178; esters, such as ethyl acetate, and as further described in U.S. Pat. No. 6,824,671; alcohol alkoxylates, such as glycol ethers, e.g. ethylene glycol monomethyl ether(2-methoxyethanol) and propylene glycol monoethyl ether and ethoxylates derived from mixed $C_2$ to $C_{24}$, preferably $C_2$ to $C_{18}$ and most preferably $C_6$ to $C_{12}$ straight chain alcohols, and as further described in U.S. Pat. No. 5,068,487; ethers, such as dimethyl ether, diethyl ether and methyl ethyl ether; ketones; aldehydes; and alkyl halides. Protic promoters form a catalyst complex with the boron trifluoride, and such complex serves as a catalyst for the oligomerization. The complex usually contains an excess of boron trifluoride, which is adsorbed in the mixture.

Solvents or diluents may be used in the Lewis acid catalyzed copolymerization. If the catalyst system being used is a liquid, this may also function as the solvent or diluent for the reaction so that no additional solvent or diluent may be required. Additional liquids that are non-reactive to the selected catalyst system may be used as needed to control viscosity of the reaction mixture or to carry off heat of reaction by evaporation with reflux of the condensed vapor, if desired. Hydrocarbons such as alkanes and aromatics, e.g., hexane and toluene, are suitable for this purpose. Thus, a light alpha-olefin oligomer reactant, either alone or with additional alpha-olefin co-feed, may be oligomerized directly in the presence of the catalyst system with or without the addition of solvent or diluent. The reactions will normally be carried out in a closed environment if gaseous catalysts such as boron trifluoride are used. Such reactions are usually carried out under an inert atmosphere, e.g., nitrogen.

The temperature of the Lewis acid-catalyzed copolymerization reactions can usefully vary in practical operation from −10° C. to 300° C. and preferably between 0° C. to 75° C. The system may operate under atmospheric pressure as the system typically exhibits low vapor pressures at normal processing temperatures. The system may, however, be operated under mild pressure if it is desired to maintain a closed reaction environment, e.g. under autogenous pressure. When using a solid Lewis acid as the catalyst, the copolymerization will normally be carried out using a fixed bed of the catalyst in a downflow mode although alternative forms of operation, e.g., in a stirred tank reactor, are possible.

Following completion of the copolymerization reaction, the catalyst activity may be quenched by addition of water or a dilute aqueous base such as 5 wt % NaOH solution. The organic layer may be separated and distilled to remove components other than the base stock. When promoted $BF_3$ catalyst is used, the gaseous $BF_3$ and promoter may be recycled if not deactivated at the end of the reaction. When a solid catalyst is used, a simple filtration is all that is needed to separate the catalyst from the copolymer product if the reaction has not been carried out in a fixed bed. The copolymer product may then be fractionated to remove any unreacted light olefin and the copolymer in the desired boiling range, and, optionally, sent for hydrogenation to remove any residual unsaturation that may be present in the product.

The lube range copolymer product from the Lewis acid catalyzed step is desirably hydrogenated prior to use as a lubricant base stock in order to remove any residual unsaturation and to stabilize the product. The hydrogenation may be carried out in the manner conventional to the hydrotreating of conventional PAOs using, for example, a metal (usually a noble metal) hydrogenation catalyst.

A typical synthesis of the copolymer by anionic or base catalyst can be achieved as following. An alcohol or a mixture of alcohols containing poly-alpha-olefin components (PAO-alcohol) are used in this procedures. Synthesis of this type of alcohol is described below. An alcohol of 3.5 moles and 0.1 moles of potassium hydroxide available in 45% aqueous solution are mixed together in an autoclave. The mixture is heated to 105° C. under vacuum followed by purging with nitrogen to remove the water or any volatile components. The residual mixture is then heated to 140° C. The reactor pressure is adjusted to 40 psig. Ethylene oxide (618.6 gram, 14 mole) is the added continuously over one hour. The reaction continues for another 6 hours at constant temperature and stirring. The reactor is then cooled down to room temperature and subjected to vacuum for one hour. The residual oil is then diluted with heptane and washed with dilute HCl and water until wash comes out clear. Alternatively, at the end of the reaction, the reaction mixture is quenched with 5 grams water and pass through an acidic silica gel or alumina column or acidic clay to absorb all potassium hydroxide or other impurity. The filtered oil is suitable as a high performance lube base stock. Alternatively, a hydrotreating process is used to decolorize the lube oil.

In this process, the base catalyst can be any suitable base, including Group IA, IIA, IB, IIB, metal oxide or hydroxides, such as sodium hydroxide, potassium hydroxides. Group VIII metal oxides with base character are also suitable. Sometimes Group IA, IIA, IB and IIB metals are also used, although they are more expensive. The process can be run in batch or in a continuous stir-tank reactor. The metal hydroxides can be present in pure powder form or in aqueous solution of any suitable concentration. Solution form may be more suitable because it allows more contact and a more thorough reaction thus resulting in higher efficiency. A solvent can be used in the process. Typical solvents include hexanes, heptane, benzene, toluene, xylene, Norpar or Isopar solvents, and the like. More polar solvents such as tetrahydrofuran, dimethylformamide (DMF), dimethyl sulfoxide (DMSO), acetonitrile, and the like can be added as a co-solvent or as a solvent alone.

In the copolymerization process, any of the alkylene oxides discussed earlier, alone or in a mixture, can be used. If two or more alkylene oxides are added simultaneously, a block of random alkylene oxide copolymer is formed from the PAO-alcohol initiator. An example is ethylene oxide and propylene oxide copolymer block or ethylene oxide and butylene oxide copolymer. The presence of a small amount of propylene oxide or butylene oxide can be beneficial. If one alkylene oxide added first and allowed to react to completion, then a second alkylene oxide is added to react to completion. The resulting polyalkylene oxide fraction is a block copolymer.

The PAO alcohol used in this anionic or base-catalyzed method can be derived by any of several methods. In the simplest form, a Guerbet alcohol derived from a primary alcohol of n-$C_6$ to $C_{16}$ [For Guerbet chemistry, see Journal of Surfactant and Detergent, Vol. 4, No. 3, July 2001, page 311-315, or Guerbet reaction of cetyl alcohol, Journal of Applied Chemistry, Vol. 4, Issue 12, p. 637-641]. These types of alcohol are equivalent to primary alcohol derived from an alpha-olefin dimer. Alternatively, these alcohols can be synthesized from unhydrogenated alpha-olefin oligomers or polymers by any conventional alcohol synthesis method. The unhydrogenated alpha-olefin oligomers or polymers can be made according to any of the processes disclosed in U.S. Pat. Nos. 4,990,709; 4,827,064; 4,827,073; 5,012,020; and 5,264,642, which are incorporated herein by reference. Alternatively, the unhydrogenated oligomers can be made according to WO 2007011462, WO 2007011459, which are incorporated herein by reference. These oligomers as synthesized have one double bond. That double bond can be used to convert into alcohol functional group using known methods, most commonly a hydroformylation reaction. In this reaction, the olefin is reacted with synthesis gas, $CO/H_2$, catalyzed by Rh, Co, or Ru, type catalyst. The hydroformylation reaction is well known in commercial processes to produce 1-alkanols from olefins. Alternatively, the alcohol can be produced by a hydroboration reaction or oxidation with peroxides. Any of these known methods are suitable. Commercially, the Guerbet reaction and the hydroformylation of unhydrogenated PAO are useful.

Alternatively, the copolymer can be made using metal complexes as catalysts. An example is using double metal cyanides (DMC). Teachings to the use of DMC catalysts can be found in U.S. Patent Application Publication Nos. 20050256014 and 20060223979, which are incorporated herein by reference. PAO alcohols useful in the aforementioned processes can be prepared as described further above.

The copolymer may be admixed with other lubricant base stocks with which they are soluble or miscible. Useful blending base stocks include mPAOs, PAOs, GTL (gas-to-liquid materials), Group I, Group II, and Visom (Group III) base stocks. PAO base stocks are disclosed, for example, in U.S. Published Application No. 2008/0177121 A1, which is incorporated herein by reference. GTL base stocks are disclosed, for example, in U.S. Published Application No. 2007/0265178 A1, which is incorporated herein by reference. The copolymer may be admixed with other (different) lubricant base stocks in any proportion, such as 1 wt % to 99 wt % copolymer and 99 wt % to 1 wt % other lubricant base stocks (and any proportion in between) based on the total weight thereof. Preferred blends have 0.5 wt % copolymer and 99.5 wt % other lubricant base stocks, more preferably 5 wt % to 95 wt %, and most preferably 20 wt % to 80 wt % based on the total weight thereof.

The following are examples of the present disclosure and are not to be construed as limiting.

EXAMPLES

Example 1

Copolymerization of 1-decene and 1,2-epoxybutane Using $AlCl_3$ as a Catalyst

A copolymer was prepared according to the following:
Charged $AlCl_3$ (1.33 g, 0.01 mole) and 5 ml decane under $N_2$ to a three-neck round bottom flask equipped with a mechanical stirrer. Slowly added 1-decene (11.2 g, 0.08 mole) and 1,2-epoxybutane (1.44 grams, 0.02 mole) with syringe at room temperature. After addition, the reaction mixture was stirred overnight at room temperature. The reaction was stopped by adding 25 ml water and 100 ml methyl tert-butyl ether (MTBE). The MTBE layer was washed with water (2×75 ml) and (1×75 ml) brine until the aqueous layer attained pH ~7. The MTBE layer was separated and dried over anhydrous $MgSO_4$ and filtered. The low boiling (MTBE) component was then removed by using a rotary evaporator and high boiling components (decane and unreacted 1-decene) with an air bath oven at 160° C.-170° C. under vacuum. The final product yield was 47%.

The copolymer was characterized using IR, NMR and GPC. The IR spectra of polymer showed characteristic absorption peaks due to PAO (720 $cm^{-1}$, alkane with >4 $CH_2$ groups) as well as polyether. The NMR spectrum suggests that 17 mole % polyether was present in the product. The GPC gave a monomodel peak with $M_n$ 1448, $M_w$ 3062 using polystyrene standards.

The kinematic viscosity (Kv) of the liquid product was measured using ASTM standards D445 and reported at temperatures of 100° C. (Kv at 100° C.) or 40° C. (Kv at 40° C.). The viscosity index (VI) was measured according to ASTM standard D2270 using the measured kinematic viscosities for each product. The viscosity of copolymer was 29.2 cSt at 100° C. and 279.2 cSt at 40° C. with viscosity index (VI) of 140. The data suggests that the lubricant properties of the copolymers are comparable to those of PAO base stock.

TABLE 1

Lube Properties of Example 1 and PAO 30

| Sample # | $Kv_{100}$ | Viscosity Index (VI) |
|---|---|---|
| Example 1. PAO-PAG Copolymer | 29.2 | 140 |
| PAO 30 | 30 | 144 |

The friction coefficient of the PAO-PAG copolymer base stock was measured using an HFRR test (high frequency reciprocating rig) at the following conditions: 0.1 m/s (60 Hz) speed, 100° C. temperature, 1 GPa (400 grams) pressure, and a duration of 4 hours. The friction coefficient of the PAO-PAG copolymer was 0.018, while the friction coefficient of 30 cSt PAO at the same measurement conditions was 0.09.

TABLE 2

The Friction Coefficient of Example 1 and PAO 30

| Sample # | Friction Coefficient (FC) |
|---|---|
| Example 1. PAO-PAG Copolymer | 0.018 |
| PAO 30 | 0.090 |

Example 2

Synthesis of PAO-PAG Hybrid Molecule by Radical Chemistry

Decene-1, 76 grams (0.54 mole), was reacted with ethylene oxide (EO), 24 grams (0.54 mole), in the presence of a radical initiator, di-t-butyl peroxide, 5 grams, at a temperature above 100° C. in an autoclave with stirring for 16 hours. The reaction mixture was distilled under high vacuum to remove a light fraction. The resulting residual fraction contained a lube fraction with an average composition of $(C10)_2$-$(EO)_2$—H.

Example 3

Synthesis of a PAO-PAG Hybrid Molecule by $BF_3$ Catalyst

Decene-1, 76 grams (0.54 mole), was reacted with ethylene oxide (EO), 24 grams (0.54 mole), in the presence of promoted $BF_3$ catalyst, at a temperature above 20° C. in an autoclave with stirring for 16 hours. The reaction mixture was washed with water to remove any residual catalyst. The organic layer was distilled under high vacuum to remove a light fraction. The resulting residual fraction contained a lube fraction with an average composition of $(C_{10})_2$-$(EO)_2$—H.

Example 4

Synthesis of PAO-PAG Hybrid Molecule by $AlCl_3$ Catalyst

Decene-1, 76 grams (0.54 mole), was reacted with ethylene oxide (EO), 24 grams (0.54 mole), in the presence of 5 grams of promoted $AlCl_3$ catalyst, at a temperature above 20° C. in an autoclave with stirring for 16 hours. The reaction mixture was washed with water to remove any residual catalyst. The organic layer was distilled under high vacuum to remove a light fraction. The resulting residual fraction contained a lube fraction with average composition of $(C_{10})_2$-$(EO)_2$—H.

Examples 5 to 10 and Comparative Examples 1 and 2

Synthesis of PAO-PAG Hybrid Molecule from PAO-Alcohol and EO

The PAO-alcohol can be any of $C_{10}$, $C_{12}$ and $C_{14}$ alcohols produced from ethylene oligomerization by a trialkylaluminum process followed by oxidative cleavage. $C_{10}$, $C_{12}$ and $C_{14}$ alcohols can be obtained from hydrogenation of corresponding fatty acids or triglycerides. A $C_{10}$-alcohol can be dimerized in the presence of Ni-on-kieselguhr catalyst in a typical Guerbet alcohol synthesis route to give $C_{20}$-alcohol. The $C_{20}$ alcohol can react with 2 moles of EO with a base catalyst to give $C_{20}$-$(EO)_2$—H lube according to the following equation:

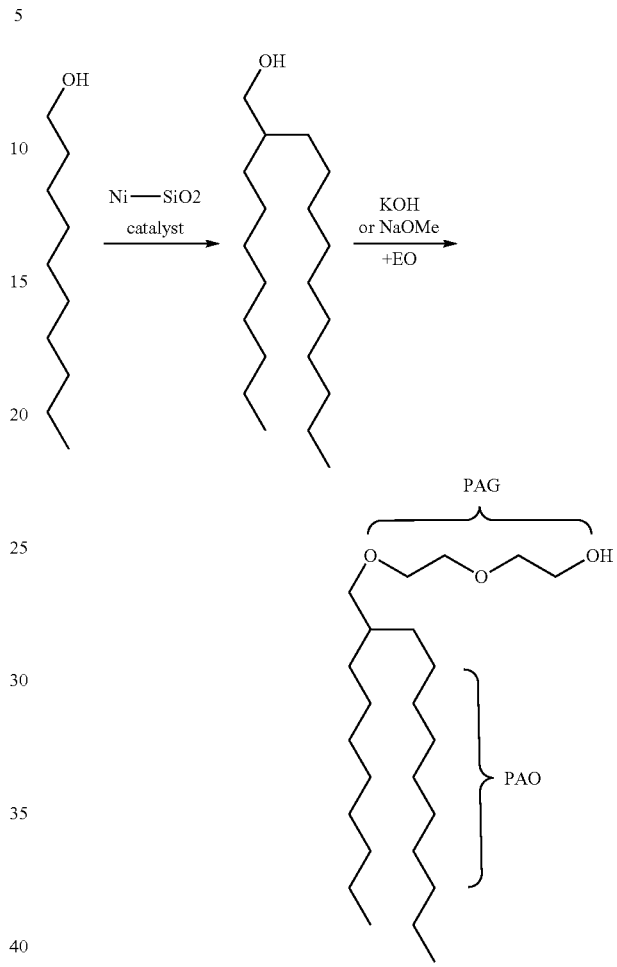

The compositions in Examples 5 to 18 exhibited high VI and low pour points. The lube fractions also exhibited low traction coefficients and low frictional coefficients, excellent wear properties under the 4-ball wear test, FZG test or the Falex seizure load test. The resulting fluids were used as base stocks for 0W20 or 0W30 automotive engine lubricant formulation resulting in improved energy efficiency improvement.

A series of PAO-PAG copolymer fluids were synthesized using the anionic method. The composition and the fluid properties are summarized in the following Table 3.

TABLE 3

| | Example | | | | | | Comp. Ex. 1 | Comp. Ex. 2 |
|---|---|---|---|---|---|---|---|---|
| | 5 | 6 | 7 | 8 | 9 | 10 | | |
| Type of AO | ethylene oxide | ethylene oxide | ethylene oxide | hexyl oxide | octyl oxide | octyl oxide | PAO5 | PAO4 |
| Alcohol | C12—OH[a] | C18—OH[b] | C20—OH[c] | C20—OH[c] | C20—OH[c] | C20—OH[c] | | |
| Average Mole Ratio AO/alcohol | 4 | 2 | 3 | 1.5 | 1.5 | 2 | | |
| Lube | | | | | | | | |

TABLE 3-continued

| | Example | | | | | | | |
|---|---|---|---|---|---|---|---|---|
| | 5 | 6 | 7 | 8 | 9 | 10 | Comp. Ex. 1 | Comp. Ex. 2 |
| Property | | | | | | | | |
| 100° C. Kv, cS | 4.17 | 4.08 | 2.7 | 4.41 | 5.06 | 6.09 | 5 | 4 |
| VI | 132 | 116 | 127 | 86 | 115 | 125 | 130 | 126 |
| Pour Point, ° C. | 3 | 15 | −48 | −64 | −51 | −60 | −55 | −66 |
| Friction Coefficient[c] | 0.065 | 0.066 | 0.14 | 0.12 | 0.13 | 0.13 | 0.17 | 0.21 |

[a] n-$C_{12}$ alcohol
[b] Oleyl alcohol
[c] 2-Octyl-n-dodecanol

As depicted in Table 3, the PAO-PAG copolymers of Examples 5 to 10 exhibit good viscometrics and lower friction coefficients than PAO alone. In addition, Examples 5 to 10 are all compatible with hydrocarbon base stocks of Group I to Group IV base stocks.

Furthermore, when the fluid of Example 5 was blended with a high quality Gr III base stock made from hydroisomerization of slack wax, the blends all exhibited significantly reduced friction coefficients compared to a control without the copolymer. Further unexpectedly, even 2% of the fluid of Example 5 exhibited a significantly reduced friction coefficient. Viscosity and friction coefficiency data are summarized in Table 4 below.

TABLE 4

| Wt % Ex. 5 in Group III base stock | Kv at 100° C., cS | Kv at 40° C., cS | VI | Friction Coefficient |
|---|---|---|---|---|
| 0 | 3.75 | 15.06 | 143 | 0.168 |
| 2 | 3.72 | 14.54 | 151 | 0.115 |
| 5 | 3.63 | 14.57 | 138 | 0.106 |
| 10 | 3.59 | 14.97 | 124 | 0.102 |
| 15 | 3.6 | 15.27 | 119 | 0.092 |
| 20 | 3.59 | 15.75 | 110 | 0.079 |
| 40 | 3.73 | 16.78 | 110 | 0.062 |
| 60 | 3.86 | 17.45 | 114 | 0.066 |
| 80 | 3.98 | 18.04 | 118 | 0.060 |
| 100 | 4.16 | 18.61 | 116 | 0.065 |

Example 11

Co-Polymerization of 1-decene and 1,2-epoxybutane Using $AlCl_3$ as a Catalyst

Charged $AlCl_3$ (2.99 g, 0.02 mole) and 40 ml methylene chloride under nitrogen in a three-neck round bottom flask equipped with mechanical stirrer. Slowly added 1-decene (22.4 g, 0.16 mole) and 1,2-epoxybutane (2.88 g, 0.04 mole) with stirring at room temperature. After addition, the reaction mixture was stirred overnight at room temperature. The reaction was stopped by adding 50 ml water and 100 ml methylene chloride. The methylene chloride layer was washed with water (2×100 ml) and (1×100 ml) brine until the aqueous layer attained pH ~7. The methylene chloride layer was separated and dried over anhydrous $MgSO_4$ and filtered. The low boiling components (methylene chloride and 1,2-epoxybutane) were then removed by using a rotary evaporator and high boiling components (1-decene and homo polymer of 1,2-epoxybutane) in an air bath oven at 160° C.-170° C. under 1 mm vacuum. The final product yield was 42%.

The copolymer was characterized using IR, NMR and GPC. The IR spectra of polymer showed characteristic absorption peaks due to PAO (721 $cm^{-1}$, alkane with >4 $CH_2$ groups) as well as other peaks at 33618, 2940, 2840, 1467, 1370, 1105, and 721 $cm^{-1}$. The NMR spectrum suggest that 3 mole % polyether was present in the product. The GPC gave a monomodel peak of $M_n$ 2556 and $M_w$ 6974 using polystyrene standards.

The kinematic viscosity (Kv) of the liquid product was measured using ASTM standards D445 and reported at temperatures of 100° C. (Kv at 100° C.) or 40° C. (Kv at 40° C.). The viscosity index (VI) was measured according to ASTM standard D2270 using the measured kinematic viscosities for each product. The viscosity of the copolymer was 83.8 cSt at 100° C. and 980 cSt at 40° C. with a viscosity index (VI) of 168. The data suggest that the lubricant properties of the copolymers are comparable to PAO base stock. The friction coefficient of the PAO-PAG copolymer base stock was measured using an HFRR test (high frequency reciprocating rig) at the following conditions: 0.1 m/s (60 Hz) speed, 32-195° C. temperature range, and 1 GPa (400 grams) pressure. The average friction coefficient of the PAO-PAG copolymer was 0.083.

Example 12

Co-Polymerization of 1-decene and 1,2-epoxybutane Using $AlCl_3$ as a Catalyst

Charged $AlCl_3$ (6.65 g, 0.05 mole) and 20 ml decane under nitrogen in a three-neck round bottom flask equipped with mechanical stirrer. Slowly added 1-decene (56 g, 0.4 mole) and 1,2-epoxybutane (7.2 g, 0.1 mole) with stirring at room temperature. After addition, the reaction mixture was stirred overnight at room temperature. The reaction was stopped by adding 75 ml water and 150 ml methylene chloride. The methylene chloride layer was washed with water (2×100 ml) and (1×100 ml) brine until the aqueous layer attained pH ~7. The methylene chloride layer was separated and dried over anhydrous $MgSO_4$ and filtered. The low boiling components (methylene chloride and 1,2-epoxybutane) were then removed by using a rotary evaporator and high boiling components (1-decene and homo polymer of 1,2-epoxybutane) with an air bath oven at 160° C.-170° C. under 1 mm vacuum. The final product yield was 27%.

The copolymer was characterized using IR, NMR and GPC. The IR spectra of polymer showed characteristic absorption peaks due to PAO (720 $cm^{-1}$, alkane with >4 $CH_2$ groups) as well as other peaks 3472, 2960, 2847, 1463, 1383, 1091, 720 $cm^{-1}$. The NMR spectrum suggests that 20 mole % polyether was present in the product. The viscosity of copolymer was 26 cSt at 100° C. and 221.4 cSt at 40° C. with viscosity index (VI) of 150. The pour point of the product was −45° C. The data suggest that the lubricant properties of the copolymers are comparable to PAO base stock. The friction coefficient of the PAO-PAG copolymer base stock was measured using an HFRR test (high frequency reciprocating rig) at the following conditions: 0.1 m/s (60 Hz) speed, 32-195° C. temperature range, and 1 GPa (400 grams) pressure. The average friction coefficient of the PAO-PAG copolymer was 0.075.

Example 13

Co-Polymerization of 1-decene and 1,2-epoxybutane Using $AlCl_3$ as a Catalyst

Charged $AlCl_3$ (1.33 g, 0.01 mole) and 5 ml decane under nitrogen in a three-neck round bottom flask equipped with a mechanical stirrer. Slowly added 1-decene (11.2 g, 0.08 mole) and 1,2-epoxybutane (1.44 g, 0.02 mole) with stirring at room temperature. After addition, the reaction mixture was stirred for overnight at room temperature. The reaction was stopped by adding 25 ml water and 100 ml tert-butyl methyl ether. Tert-butyl methyl ether layer was washed with water (2×75 ml) and (1×75 ml) brine until the aqueous layer attained pH ~7. The methylene chloride layer was separated and dried over anhydrous $MgSO_4$ and filtered. The low boiling components (tert-butyl methyl ether and 1,2-epoxybutane) was then removed by using a rotary evaporator and high boiling components (decane, 1-decene and homo polymer of 1,2-epoxybutane) with an air bath oven at 160° C.-170° C. under 1 mm vacuum. The final product yield was 47%.

The copolymer was characterized using IR, NMR, and GPC. The IR spectra of the copolymer showed characteristic absorption peaks at 3472, 2922, 2842, 1468, 1378, 1101, and 729 $cm^{-1}$. The NMR spectrum suggests that 19 mole % polyether was present in the product. The GPC gave a monomodel peak of $M_n$ 1561 and $M_w$ 4111 using polystyrene standards. The viscosity of copolymer was 35.5 cSt at 100° C. and 317.4 cSt at 40° C. with a viscosity index (VI) of 158. The data suggest that the lubricant properties of the copolymers are comparable to PAO base stock. The friction coefficient of the PAO-PAG copolymer base stock was measured using an HFRR test (high frequency reciprocating rig) at the following conditions: 0.1 m/s (60 Hz) speed, 32-195° C. temperature range, and 1 GPa (400 grams) pressure. The average friction coefficient of the PAO-PAG copolymer was 0.04.

Example 14

Co-Polymerization of 1-decene and 1,2-epoxybutane Using $AlCl_3$ as a Catalyst

Charged $AlCl_3$ (4 g, 0.03 mole) and 25 ml methylene chloride under nitrogen in a three-neck round bottom flask equipped with a mechanical stirrer. Slowly added 1-decene (33.6 g, 0.24 mole) and 1,2-epoxybutane (4.32 g, 0.06 mole) with stirring at room temperature. After addition, the reaction mixture was stirred overnight at room temperature. The reaction was stopped by adding 25 ml water and 100 ml methylene chloride. The methylene chloride layer was washed with water (2×75 ml) and (1×75 ml) brine until the aqueous layer attained pH ~7. The methylene chloride layer was separated and dried over anhydrous $MgSO_4$ and filtered. The low boiling components (methylene chloride and 1,2-epoxybutane) were then removed by using a rotary evaporator and high boiling components (1-decene and homo polymer of 1,2-epoxybutane) with an air bath oven at 160° C.-170° C. under 1 mm vacuum. The final product yield was 84%.

The copolymer was characterized using IR, NMR, and GPC. The IR spectra of polymer showed characteristic absorption peaks at 3454, 2917, 2847, 1468, 1369, 1091, and 725 $cm^{-1}$. The NMR spectrum suggests that 6.3 mole % polyether was present in the product. The viscosity of the copolymer was 92.5 cSt at 100° C. and 1030 cSt at 40° C. with a viscosity index (VI) of 178. The pour point of the product was −36° C. The data suggest that the lubricant properties of the copolymers are comparable to PAO base stock. The friction coefficient of the PAO-PAG copolymer base stock was measured using an HFRR test (high frequency reciprocating rig) at the following conditions: 0.1 m/s (60 Hz) speed, 32-195° C. temperature range, and 1 GPa (400 grams) pressure. The average friction coefficient of the PAO-PAG copolymer was 0.11.

Example 15

Co-Polymerization of 1-decene and 1,2-epoxybutane Using $AlCl_3$ as a Catalyst

Charged $AlCl_3$ (4 g, 0.03 mole) and 25 ml decane under nitrogen in a three-neck round bottom flask equipped with a mechanical stirrer. Slowly added 1-decene (33.6 g, 0.24 mole) and 1,2-epoxyhexane (6.2 g, 0.06 mole) with stirring at 50° C. After addition, the reaction mixture was stirred for 4 hours at 50° C. and then allowed to cool to room temperature. The reaction was stopped by adding 25 ml water and 100 ml methylene chloride. The methylene chloride layer was washed with water (2×75 ml) and (1×75 ml) brine until the aqueous layer attained pH ~7. The methylene chloride layer was separated and dried over anhydrous $MgSO_4$ and filtered. The low boiling components (methylene chloride and 1,2-epoxybutane) were then removed by using a rotary evaporator and high boiling components (1-decene and homo polymer of 1,2-epoxybutane) with an air bath oven at 160° C.-170° C. under 1 mm vacuum. The final product yield was 70%.

The copolymer was characterized using IR, NMR, and GPC. The IR spectra of polymer showed characteristic absorption peaks due to PAO (721 $cm^{-1}$, alkane with >4 $CH_2$ groups) as well as other peaks 3583, 2955, 2923, 2853, 1464, 1377, 1301, 1098, and 721 $cm^{-1}$. The NMR spectrum suggests that 9.01 mole % polyether was present in the product. The viscosity of the copolymer was 31.4 cSt at 100° C. and 270.4 cSt at 40° C. with a viscosity index (VI) of 157. The pour point of the product was −42° C. The data suggest that the lubricant properties of the copolymers are comparable to PAO base stock. The friction coefficient of the PAO-PAG copolymer base stock was measured using an HFRR test (high frequency reciprocating rig) at the following conditions: 0.1 m/s (60 Hz) speed, 32-195° C. temperature range, and 1 GPa (400 grams) pressure. The average friction coefficient of the PAO-PAG copolymer was 0.12.

Example 16

Co-Polymerization of 1-decene and 1,2-epoxybutane Using $AlCl_3$ as a Catalyst

Charged $AlCl_3$ (10.64 g, 0.08 mole) and 25 ml methylene chloride under nitrogen in a three-neck round bottom flask equipped with a mechanical stirrer. Slowly added 1-decene (28 g, 0.2 mole) and 1,2-epoxyhexane (14.4 g, 0.2 mole) with stirring at 0° C. After addition, the reaction mixture was stirred for 4 hours at 0° C. The reaction was stopped by adding 50 ml water and 300 ml methylene chloride. The methylene chloride layer was washed with water (2×100 ml) and (1×100 ml) brine until the aqueous layer attained pH ~7. The methylene chloride layer was separated and dried over anhydrous $MgSO_4$ and filtered. The low boiling components (methylene chloride and 1,2-epoxybutane) were then removed by using a rotary evaporator and high boiling components (1-decene and homo polymer of 1,2-epoxybutane) with an air bath oven at 160° C.-170° C. under 1 mm vacuum. The final product yield was 64%.

The copolymer was characterized using IR, NMR, and GPC. The IR spectra of polymer showed characteristic absorption peaks due to PAO (721 $cm^{-1}$, alkane with >4 $CH_2$ groups) as well as other peaks 3471, 2955, 2852, 1464, 1377, 1095, and 721 $cm^{-1}$. The NMR spectrum suggests that 24.8 mole % polyether was present in the product. The GPC gave a monomodel peak of $M_n$ 3118 and $M_w$ 6369 using polystyrene standards. The viscosity of copolymer was 46.1 cSt at 100° C. and 472 cSt at 40° C. with a viscosity index (VI) of 154. The pour point of the product was −39° C. The data suggest that the lubricant properties of the copolymers are comparable to PAO base stock.

Example 17

Co-Polymerization of 1-decene and 1,2-epoxyhexane Using $AlCl_3$ as a Catalyst

Charged $AlCl_3$ (5.32 g, 0.04 mole) and 25 ml 1,2-dichloroethane under nitrogen in a three-neck round bottom flask equipped with a mechanical stirrer. Slowly added 1-decene (14 g, 0.1 mole) and 1,2-epoxyhexane (10 g, 0.1 mole) with stirring at 50° C. After addition, the reaction mixture was stirred for 4 hours at 50° C. and then the reaction mixture was allowed to cool to room temperature. The reaction was stopped by adding 25 ml water and 100 ml methylene chloride. The methylene chloride layer was washed with water (2×75 ml) and (1×75 ml) brine until the aqueous layer attained pH ~7. The methylene chloride layer was separated and dried over anhydrous $MgSO_4$ and filtered. The low boiling components (methylene chloride and 1,2-epoxybutane) was then removed by using a rotary evaporator and high boiling components (1-decene and homo polymer of 1,2-epoxybutane) with an air bath oven at 160° C.-170° C. under 1 mm vacuum. The final product yield was 64%.

The copolymer was characterized using IR, NMR, and GPC. The IR spectra of the copolymer showed characteristic absorption peaks due to PAO (723 $cm^{-1}$, alkane with >4 $CH_2$ groups) as well as other peaks 3454, 2955, 2854, 1463, 1377, 1102, and 723 $cm^{-1}$. The NMR spectrum suggests that 9.2 mole % polyether was present in the product. The GPC gave a $M_n$ 1309 and $M_w$ 3174 using polystyrene standards. The viscosity of copolymer was 39.4 cSt at 100° C. and 486 cSt at 40° C. with a viscosity index (VI) of 127. The pour point of the product was −39° C. The data suggest that the lubricant properties of the copolymers are comparable to PAO base stock.

Example 18

Co-Polymerization of 1-decene and 1,2-epoxybutane Using $AlCl_3$ as a Catalyst

Charged $AlCl_3$ (17.02 g, 0.128 mole) and 25 ml decane under nitrogen in a three-neck round bottom flask equipped with a mechanical stirrer. Slowly added 1-decene (44.8 g, 0.32 mole) and 1,2-epoxybutane (23 g, 0.32 mole) with stirring at room temperature. After addition, the reaction mixture was stirred for 4 hours at room temperature. The reaction was stopped by adding 100 ml water and 200 ml toluene. The toluene layer was washed with water (2×100 ml) and (1×100 ml) brine until the aqueous layer attained pH ~7. The methylene chloride layer was separated and dried over anhydrous $MgSO_4$ and filtered. The low boiling components (toluene and 1,2-epoxybutane) was then removed by using a rotary evaporator and high boiling components (1-decene and decane) with an air bath oven at 160° C.-170° C. under 1 mm vacuum. The final product yield was 65.7%.

The copolymer was characterized using IR, NMR, and GPC. The IR spectra of the copolymer showed characteristic absorption peaks due to PAO (721 $cm^{-1}$, alkane with >4 $CH_2$ groups) as well as other peaks 3453, 2955, 2853, 1464, 1377, 1096, and 721 $cm^{-1}$. The NMR spectrum suggests that 11 mole % polyether was present in the product. The viscosity of the copolymer was 48.7 cSt at 100° C. and 508 cSt at 40° C. with a viscosity index (VI) of 154. The pour point of the product was −39° C. The data suggest that the lubricant properties of the copolymers are comparable to PAO base stock.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

What is claimed is:

1. A poly(alpha-olefin/alkylene glycol) copolymer of the following formula:

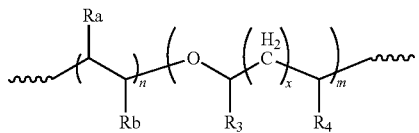

wherein $R_3$, $R_4$, Ra, and Rb are, independently, any of H, a $C_1$ to $C_{18}$ normal or branched alkyl radical, or a $C_1$ to $C_{18}$ aromatic radical or aromatic-containing alkyl radicals; wherein n and m, are, independently, integers resulting in the copolymer having a molecular weight ranging from 200 to 20,000; and wherein x is an integer from 0 to 10, wherein the copolymer is a block copolymer or a random copolymer, and wherein the alpha-olefin is a linear or branched $C_9$ to $C_{20}$ α-olefin.

2. The copolymer of claim 1, wherein n and m, are, independently, integers resulting in the copolymer having a molecular weight ranging from 300 to 10,000.

3. The copolymer of claim 1, wherein x is an integer from 0 to 5.

4. The copolymer of claim 1, wherein the copolymer is poly(1-decene/1,2-epoxybutene)copolymer.

5. The copolymer of claim 1, wherein the $C_9$ to $C_{20}$ α-olefin is selected from the group consisting of 1-nonene, 1-decene, 1-undecene, 1-dodecene, 1-tetradecene, 1-hexadecene, and combinations thereof.

6. The copolymer of claim 1, wherein the alkylene glycol has 2 to 20 carbons.

7. The copolymer of claim 6, wherein the alkylene glycol is selected from the group consisting of ethylene oxide, propylene oxide, 1,2-epoxybutane, 2,3-epoxybutane, 1,2-epoxydodecane, 1,2-epoxyhexadecane, 1,2-epoxyhexane, 1,2-epoxyoctane, 1,2-epoxypentane, 1,2-epoxytetradecane, and combinations thereof.

8. The copolymer of claim 1, wherein the alpha-olefin content is greater than the alkylene glycol content on a mole basis.

9. A lubricant formulation, comprising:
a first lubricant base stock of the copolymer of claim 1 and
a second lubricant base stock different than the first base stock.

10. The formulation of claim 8, wherein the second base stock is selected from the group consisting of a mPAO, a PAO, a GTL, a Group I, a Group II, and a Group III.

* * * * *